United States Patent
Detruit et al.

(10) Patent No.: US 7,475,776 B2
(45) Date of Patent: *Jan. 13, 2009

(54) DEVICE FOR PACKAGING AND FOLDING A FLEXIBLE MATERIAL PART, IN PARTICULAR A PARIETAL REINFORCEMENT

(75) Inventors: Bernard Detruit, Saint-Cloud (FR); Michel Therin, Lyons (FR); Pierre Bailly, Caluire (FR)

(73) Assignee: Sofradim Production, Trevoux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/824,628

(22) Filed: Jul. 2, 2007

(65) Prior Publication Data

US 2007/0245688 A1    Oct. 25, 2007

Related U.S. Application Data

(63) Continuation of application No. 10/491,715, filed as application No. PCT/FR02/03826 on Nov. 7, 2002, now Pat. No. 7,243,791.

(30) Foreign Application Priority Data

Nov. 15, 2001    (FR) .................................. 01 14804

(51) Int. Cl.
*B65D 83/10*    (2006.01)
(52) U.S. Cl. ...................................... 206/363; 206/438
(58) Field of Classification Search .............. 206/63.3, 206/227, 363, 364, 370, 438, 570–572
See application file for complete search history.

(56) References Cited

U.S. PATENT DOCUMENTS

| | | | |
|---|---|---|---|
| 4,511,035 A | 4/1985 | Alpern | |
| 4,586,930 A | 5/1986 | Kelman | |
| 4,697,703 A | 10/1987 | Will | |
| 5,284,244 A | 2/1994 | O'Toole et al. | |
| 5,392,918 A | 2/1995 | Harrison | |
| 5,972,008 A | 10/1999 | Kalinski et al. | |
| 7,243,791 B2 * | 7/2007 | Detruit et al. ............... | 206/363 |

FOREIGN PATENT DOCUMENTS

| | | |
|---|---|---|
| EP | 0 625 334 | 11/1994 |
| FR | 2771622 | 6/1999 |
| WO | WO 95/32687 | 12/1995 |

* cited by examiner

*Primary Examiner*—David T Fidei
(74) *Attorney, Agent, or Firm*—Carter, DeLuca, Farrell & Schmidt, LLP

(57) ABSTRACT

The invention concerns a device comprising: a packaging box for the flexible material part, dimensioned to hold said part flat; folding means for folding said part without direct handling; and a reception tube for receiving said folded flexible material part. The invention is characterized in that the reception tube is not longitudinally slit, and the folding means comprise; a traction suture connected to the flexible material part, which passes through the tube, and, walls forming a funnel whereof the base emerges proximate to the opening of the tube through which the flexible material part is designed to be inserted into said tube, said funnel being designed, when a traction is exerted on the traction suture, to gradually fold down the zones of the part located laterally relative to the tube towards the zone of the part located opposite the opening of said tube, to enable the part to be inserted into the tube.

14 Claims, 4 Drawing Sheets

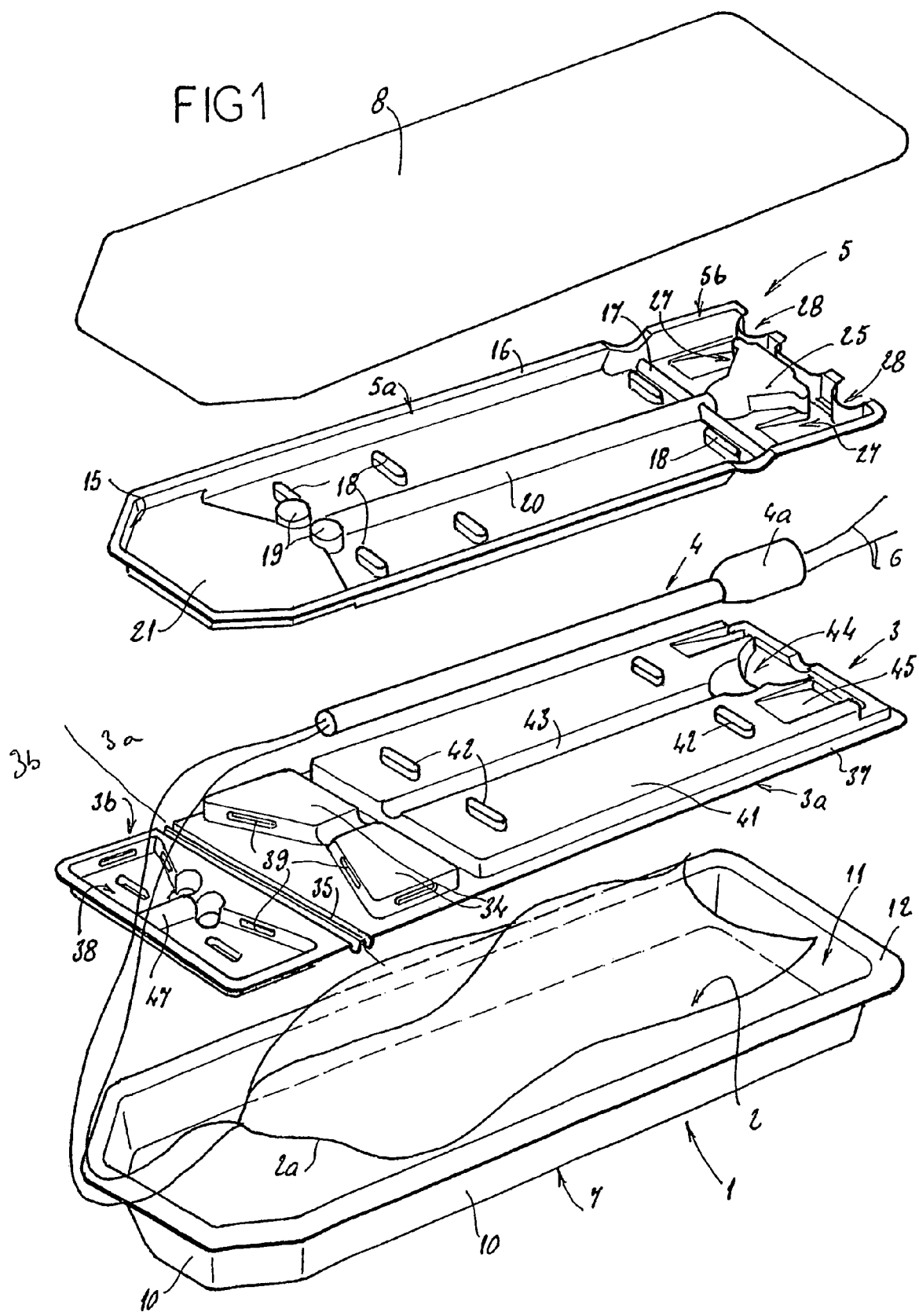

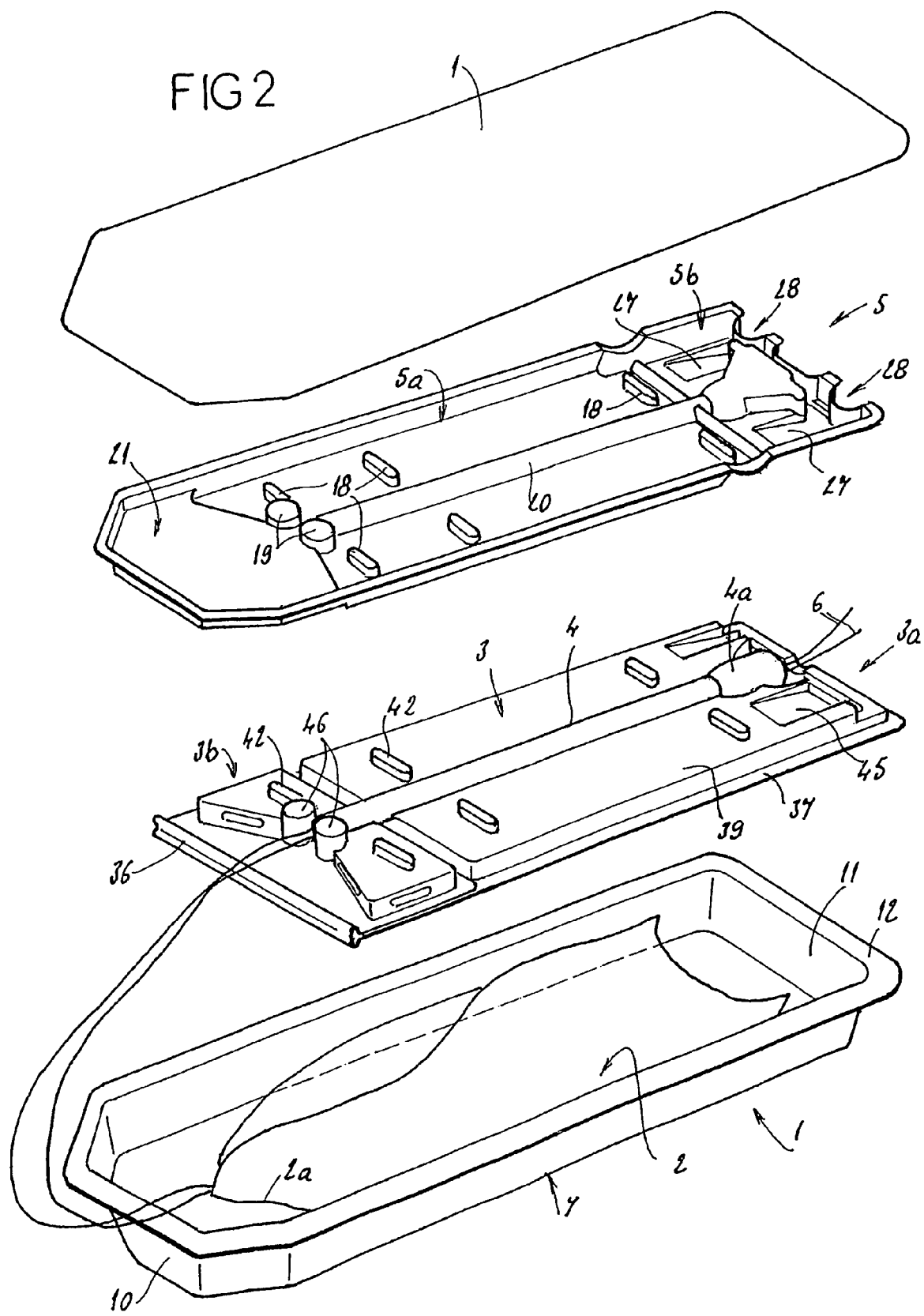

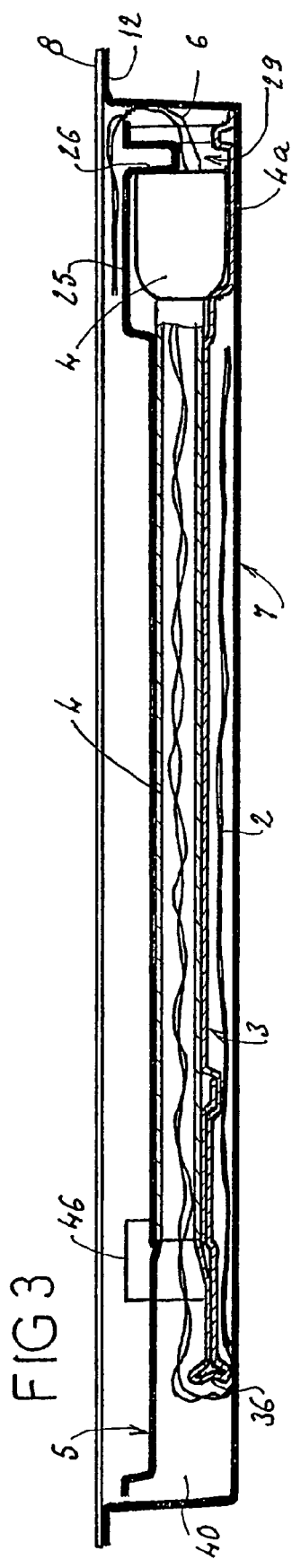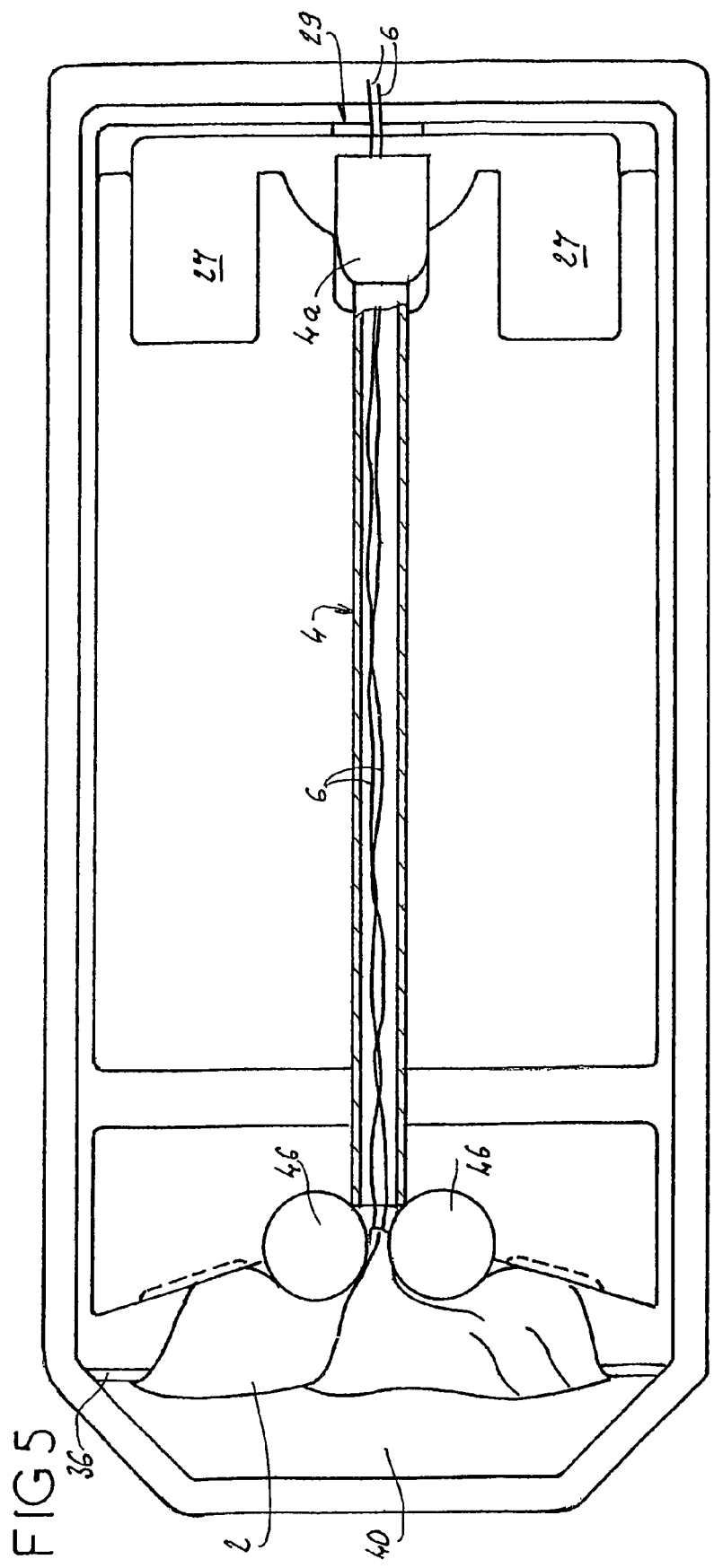

DEVICE FOR PACKAGING AND FOLDING A FLEXIBLE MATERIAL PART, IN PARTICULAR A PARIETAL REINFORCEMENT

CROSS-REFERENCE TO RELATED APPLICATIONS

This application is a continuation and claims the benefit of U.S. patent application Ser. No. 10/491,715 filed Apr. 10, 2004, now U.S. Pat. No. 7,243,791, which is a national stage application of PCT/FR02/03826 filed Nov. 7, 2002 which claims priority to French patent application No. 01/014804 filed Nov. 15, 2001, the entire content of which is incorporated by reference herein.

BACKGROUND OF THE INVENTION

1. Technical Field

The present invention relates to a device for packaging and folding a flexible material part, especially a parietal reinforcement.

2. Background of Related Art

Certain flexible material parts have to be stored flat in their protective packagings in order to avoid any alteration of their flat shape following prolonged folding or rolling up, in particular the formation of creases, then, at the point of use, have to be folded longitudinally or rolled up in such a way as to have a compact cross-sectional shape.

This is particularly the case with a parietal reinforcement designed to be fitted by means of a coelioscopy method. The reinforcement must, in fact, be arranged flat in its packaging, otherwise irreversible creases might be formed in its material, subsequently preventing the reinforcement from being placed in intimate contact with the wall to be treated, with a view to a cell colonization. At the moment of its implantation, the reinforcement must be folded for insertion into a trocar so as to be introduced into the body of the patient through a small orifice.

According to an existing method, the reinforcement is simply placed in a parallelepipedal box of suitable dimensions. This box is opened at the moment of the fitting of the reinforcement and the practitioner folds this reinforcement manually prior to inserting it into a previously fitted trocar.

This method has the drawback of involving a handling of the reinforcement and hence of generating a risk of its becoming contaminated by the gloves of the practitioner. Moreover, the reinforcement rubs against the wall of the trocar as it is inserted into the latter, which likewise risks contamination of the reinforcement if the wall of the trocar is contaminated.

French patent No. 94/12700 proposes inserting a traction suture through the reinforcement, along a crenellated or wavy path. Pulls on the ends of the suture allow a "concertina-type" folding of the reinforcement to be achieved.

This method has the advantage of avoiding direct handling of the reinforcement for achievement of the folding, of ensuring a minimum bulk size of the reinforcement prior to introduction into the trocar, and of producing a concertina-type folding, which allows the reinforcement to be unfolded as it is extracted from the trocar. On the other hand, this method still involves handlings of the reinforcement at the moment of collection from its packaging box and its introduction into the trocar. Nor does this method eliminate the risk of contamination of the reinforcement by rubbing against the wall of the trocar.

Another method likewise consists in equipping the packaging box of the reinforcement with a roll-up key connected to one of the edges of the reinforcement and with a longitudinally slit tube into which the roll-up key is placed. At the moment of fitting of the reinforcement, the key is rotated, enabling the reinforcement to be rolled up and engaged in the slit tube. This slit tube is used to introduce the reinforcement into the trocar.

This method has the advantage of eliminating all handling of the reinforcement during folding and of protecting the reinforcement from all contamination by rubbing against the wall of the trocar. On the other hand, the slit in the tube has the drawback of making the trocar non-impervious to gas when this tube is engaged through the valve provided in the proximal end of the trocar. The result is that, upon the insertion of this tube into the trocar, there is an escape of the carbon dioxide used to raise the abdominal wall of the patient in order to free the zone of implantation of the reinforcement. The latter has therefore to be introduced "blind", which is undoubtedly a constraint. The slit tube, moreover, has a relatively large outer diameter, 12 mm in size, resulting from the use of the roll-up key. This large diameter entails the use of a trocar of corresponding inner diameter, not always suited to the surgical conditions. In addition, the reinforcement is rolled up upon itself, such that it has to be fully released from the trocar in order to be able to be opened out at the implantation site; this release is a marked constraint as compared to a concertina-type folding as mentioned above, which allows the reinforcement to be opened out as it is extracted from the trocar.

The present invention aims to eliminate precisely these drawbacks.

SUMMARY

The device concerned comprises, in a manner which is known per se:
  a packaging box for the flexible material part, dimensioned so as to hold this part flat,
  folding means allowing this part to be folded without direct handling, and
  a receiving tube, designed to receive the flexible material part in the folded state.
According to the invention,
the receiving tube is not longitudinally slit, and
the folding means comprise:
  a traction suture connected to the flexible material part, which passes through the tube, and
  walls forming a funnel, the base of which emerges close to the opening in the tube through which the flexible material part is designed to be introduced into this tube, this funnel being fit, when a traction is applied to the traction suture, to progressively fold down those zones of the part which are situated laterally relative to the tube toward that zone of the part which is situated opposite the opening in this tube, to allow the part admission to the tube.

The engagement of the flexible material part in the tube is thus realized by simple traction on said traction suture, hence without any direct contact or handling of this part. The funnel-forming walls cause those zones of the part situated laterally relative to the tube to be folded toward that zone of the part which is situated opposite the opening in this tube and therefore allow the achievement of a more or less "concertina-type" folding-up of this part in this tube.

The packaging and folding device can be produced with standard materials for a packaging, at very low cost price. It can especially be produced by the assembly of parts made of thermoformed synthetic material.

The flexible material part, once inserted in the tube, is perfectly protected from contaminations upon its introduction into a trocar. This tube forms, moreover, a particularly convenient means for achieving this introduction in optimal conditions. The tube can have a relatively small diameter, especially eight millimetres, which allows it to be used with trocars of corresponding small diameters; it thus avoids recourse to a special trocar in order to realize said introduction, thereby substantially simplifying the operation. Furthermore, since it is not slit, the tube is gas-tight and does not give rise to an escape of carbon dioxide when introduced through the valve fitted to the trocar.

This tube, moreover, can itself be equipped with a proximal gas-tight valve and can, therefore, itself be used as a trocar. This possibility, apart from the simplification which it brings, helps to reduce the cost of the procedure.

Advantageously, said funnel-forming walls comprise two rounded walls defining between them a pass-through gap for the flexible material part having a width less than that of this opening in the tube.

These rounded walls prove to allow the flexible material part to be folded up perfectly. They can especially be constituted by side walls of two cylindrical blocks connected to the packaging box.

The flexible material part could, in this box, extend in the horizontal extension of the tube, which would have the drawback, however, of conferring large dimensions upon the device and of involving an increase in material. For this reason, according to a preferred embodiment of the invention, the device comprises a tray which delimits, with the packaging box, a bottom receptacle for receiving the flexible material part, comprises said funnel-forming walls on its face opposite that delimiting this receptacle, and has a rounded side edge, extending back from the box, around which the flexible material part is designed to slide when the aforesaid traction is applied to the traction suture.

This tray can comprise wedging means allowing the receiving tube to be immobilized until the flexible material part is fully engaged in this tube.

Advantageously, the device additionally comprises a cover configured such as to grip the receiving tube tightly between it and the aforesaid tray.

This cover, in conjunction with the tray, allows the receiving tube to be perfectly immobilized throughout the operation for inserting the flexible material part in this tube.

This cover can be separable from said tray to allow extraction of the receiving tube. Preferably, it comprises a hinged flap, allowing access to the receiving tube with a view to such extraction.

Advantageously, said tray or said cover, or both, can comprise a zone in the shape of an inverted "V", the base of which is situated substantially coaxially to the axis of said receiving tube, this zone being designed to be passed through by the traction suture.

This zone thus allows that portion of the traction suture which is engaged in the receiving tube to be held perfectly coaxial to this tube, whatever the angle at which the traction is applied to this suture.

For a good understanding thereof, the invention is re-described below with reference to the appended diagrammatic drawing representing, by way of non-limiting example, a preferred embodiment of the device to which it relates.

BRIEF DESCRIPTION OF THE DRAWINGS

FIG. 1 is an exploded perspective view of the parts which make it up, prior to configuration of one of these parts with a view to its assembly;

FIG. 2 is a view, similar to that of FIG. 1, of these same parts, after said configuration;

FIG. 3 is a side view of the device, in longitudinal section;

FIG. 5 is a top view during folding of a parietal reinforcement which it contains.

DETAILED DESCRIPTION OF THE PREFERRED EMBODIMENTS

Figure 6:
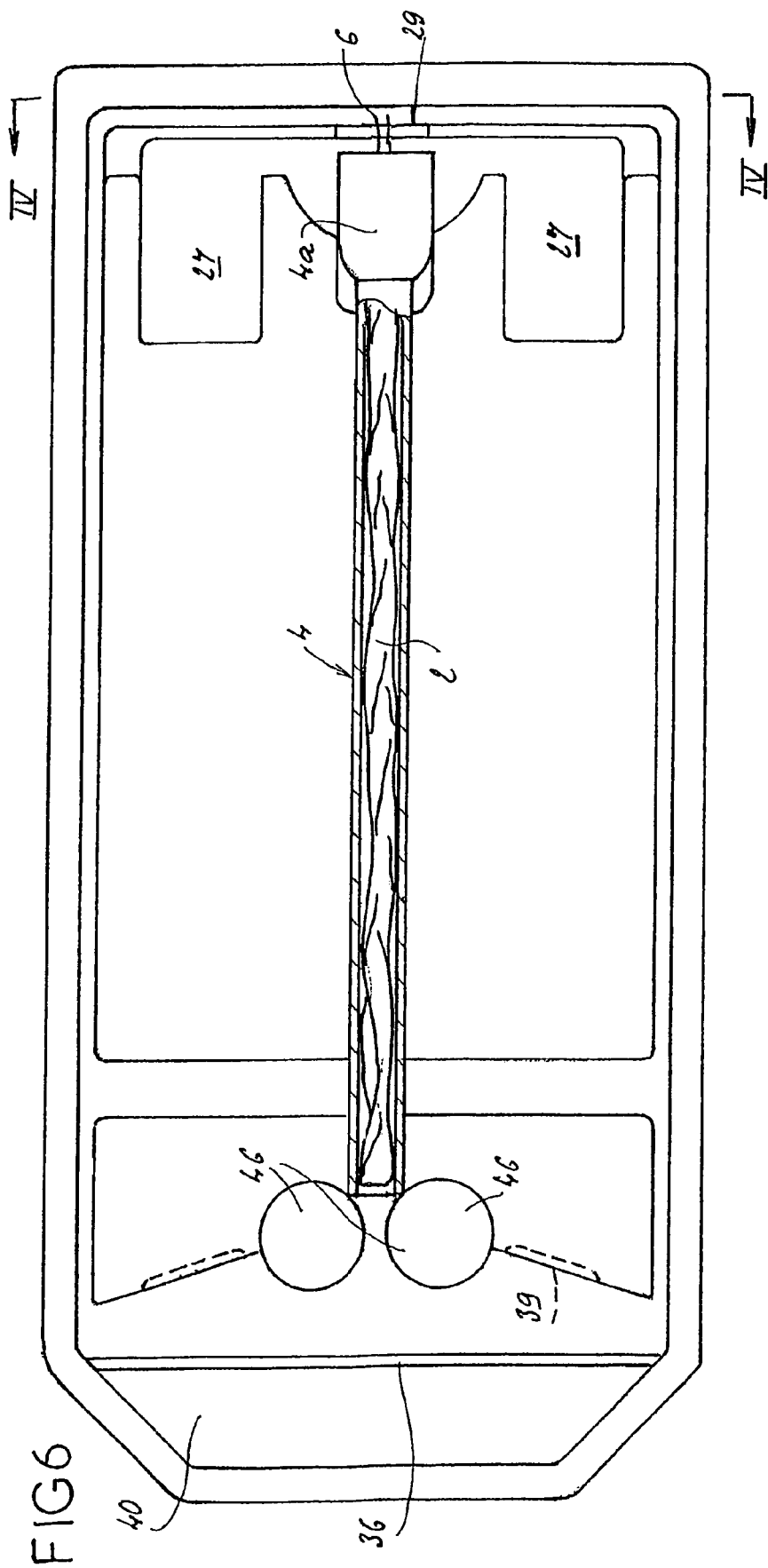
FIG. 6 is a view similar to FIG. 5, after this parietal reinforcement has been fully folded.

FIGS. 1 to 4 represent a device 1 for packaging and folding a parietal reinforcement 2, this reinforcement 2 being designed to be fitted by means of a coelioscopy method.

The reinforcement 2 is of the traditional type, especially realized in the form of a woven fabric or a knitted fabric of synthetic fibres, with openwork structure. In the example represented in the drawing, it has a substantially rectangular general form, such that it defines an end side edge 2a having a medial zone.

The device 1 comprises a packaging box for the reinforcement 2, a tray 3, a receiving tube 4 for receiving the reinforcement 2 in the flat state, a cover 5 and a traction suture 6. A supplementary packaging box (not represented), receiving the whole of the device 1, is provided so as to ensure the perfect sterility of the device.

The packaging box for the reinforcement 2 is formed by a base 7 and a lid 8.

The base 7 comprises side walls 10 delimiting a cavity 11 and an outer peripheral rim 12 situated level with the opening in the cavity 11.

The lid 8 is sealed on the rim 12 such that it can be peeled off.

The cover 5 is constituted by a part made of thermoformed synthetic material. It has walls 15, allowing it to be fitted tightly into the opening in the base 7, and a peripheral rim 16, designed to come to bear against the rim 12 upon completion of this fitting.

The cover 5 is sub-divided into a main portion 5a and a marginal portion 5b, the latter being connected to the main portion 5a along a transverse fold line 17. This line 17 forms a hinge, which allows the portion 5b to be folded upward relative to the portion 5a.

The portion 5a has six oblong blocks 18 and two cylindrical blocks 19 delimiting, on the bottom face of the cover 5, cavities designed to tightly receive corresponding respective blocks 42, 46 (cf. FIGS. 2 and 3), contained in the tray 3, so as to allow the assembly of the cover 5 and of the tray 3.

This portion 5a likewise has an elongate depression 20, which delimits a semi-cylindrical receptacle emerging on the bottom face of the cover 5, this receptacle being designed to tightly receive the tube 4, as shown in FIGS. 3 to 6. On the side opposite the portion 5b, the portion 5a has a raised wall 21.

The portion 5b has a boss 25 delimiting, on the bottom face of the cover 5, a receptacle designed to receive a widened proximal portion 4a of the tube 4. This boss 25 is bounded, on the side opposite the portion 5a, by a wall 26 perpendicular to the axis of the receptacle delimited by the depression 20 (cf. FIG. 3).

This portion 5b additionally has side cavities 27 and, on the side opposite the portion 5a, two rounded zones which delimit cavities 28. These cavities 27 and 28 are fit to receive the fingers of a user, as will become apparent later.

Figure 4:
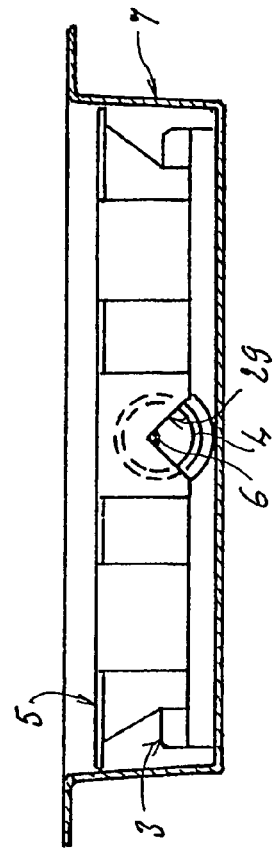
FIG. 4 is a sectional view along the line IV-IV of FIG. 6.

In addition, as shown by FIG. 4, the portion 5b has, on the side opposite the portion 5a, a notch 29 in the form of an inverted "V", the base of which aligns substantially with the axis of the receptacle delimited by the depression 20 when the portion 5b is placed in the extension of the portion 5a.

The tray 3 is likewise made of a thermoformed synthetic material. It has a main portion 3a and a marginal portion 3b mutually connected by a transverse fold line 35. This line 35 allows the portion 3b to be folded over onto the portion 3a, as can be seen by comparing FIGS. 1 and 2. This line 35 is bordered by two grooves having rounded bases, such that the folding-over of the portion 3b onto the portion 3a forms a relatively broad rounded flange 36.

It can be seen in FIGS. 1 and 2 that the portions 3a and 3b have blocks 34 and corresponding recesses 38, as well as ribs and snap-lock depressions 39, which allow the tight fitting and retention of the portion 3b on the portion 3a.

The portion 3a has a peripheral rim 37, which allows it to be positioned, with wedging, in the base 7. This portion 3a is dimensioned in such a way that the flange 36 is located back from the corresponding wall 10 of the base 7. When the tray 3 is placed in the base 7, a passage 40 therefore exists between this flange 36 and this wall 10, fit to allow the reinforcement 2 to slide through it.

The portion 3a comprises a raised central zone 41, defining a bottom receptacle for receiving the reinforcement 2. This zone 41 comprises four blocks 42, a semi-cylindrical receptacle 43 emerging in the top face of the tray 3, dimensioned so as to tightly receive the tube 4, a flared receptacle 44 dimensioned to tightly receive the portion 4a of the tube 4, and two cavities 45 designed to receive the walls delimiting the cavities 27.

For its part, the portion 3b comprises two blocks 42 and two cylindrical blocks 46, as well as a semi-cylindrical depression 47 which delimits a receptacle entering the extension of the receptacle 43 when the portion 3b is folded over onto the portion 3a. This receptacle is fit, with the receptacle delimited by the depression 20, to tightly receive the tube 4, as is shown by FIG. 2.

It can be seen, more particularly in FIGS. 5 and 6, that the two blocks 46 are arranged at a distance apart less than the inner diameter of the tube 4, such that they form a stop against which the end of the tube 4 comes to be positioned when this tube 4 is placed in the aforesaid receptacles of the tray 3 and cover 5. FIGS. 3 and 5 show, for their part, that the length of the tube 4 is such that the other end of this tube 4 reaches the immediate proximity of the wall 26. This tube 4 is thus tightly imprisoned between the cover 5 and the tray 3 when the blocks 42 and the top part of the blocks 46 are engaged in the cavities delimited by the blocks 18 and 19 and is axially jammed when the portion 5b is held applied to the tray 3. The raising of this portion 5b allows, on the other hand, the removal of the stop formed by the wall 26, so that the tube 4 can be withdrawn, by sliding, from between the cover 5 and the tray 3.

The portion 4a of the tube 4 accommodates a gas-tight shutter, of the traditional type. This shutter is fit to resist the pressure of the carbon dioxide gas used to raise the patient's abdominal wall during the procedure, which raising offers freedom of access to the site of implantation of the reinforcement 2.

The suture 6 comprises two strands forming a loop. It is connected to the medial zone of the aforesaid side edge 2a of the reinforcement 2 and passes through the tube 4. Its length is such that it can be grasped in order to apply a traction capable of making the reinforcement 2 penetrate the tube 4, as described below.

In practice, the user grasps the suture 6 by one hand and, with his other hand, applies pressure to the portion 5b, engaging his thumb and his index finger of this other hand in the cavities 27.

A traction is applied to the suture 6, causing the reinforcement 2 to pass around the flange 36 before coming into contact with the side walls of the blocks 46. This contact, as illustrated in FIG. 5, produces a gradual folding-down of the side zones of the reinforcement 2 toward the medial zone of this reinforcement, and hence a more or less concertina-type folding of the reinforcement 2.

Continuation of this traction effects the complete introduction of the reinforcement 2 into the tube 4.

In the course of this traction, the suture 6 comes to bear against the base of the notch 29, thereby ensuring that that portion of the suture 6 situated in the tube 4 is held in a position substantially coaxial to this tube 4, whatever the angle at which the user applies said traction.

Once the reinforcement 2 is fully engaged in the tube 4, the cavities 28 are utilized to raise the portion 5b of the cover 5 and thus free the tube 4, which is able to be withdrawn, by sliding, from between the cover 5 and the tray 3.

The tube 4 can then be used as a trocar for introducing the reinforcement 2 into the body of the patient.

As is evident from the above-stated, the invention provides a device for packaging and folding a flexible material part, especially a parietal reinforcement 2, which device offers the following decisive advantages:

"concertina-type" folding of the reinforcement 2, without any manual contact with the reinforcement and according to a simple movement;

insertion of the reinforcement 2 into a tube 4 of relatively small diameter, allowing the reinforcement to be protected as it is fed through a trocar;

gas-impermeability of the tube 4 and possibility of use of this tube as a trocar;

possibility of producing the device with standard packaging materials, at a very low cost price.

The invention is not, of course, limited to the embodiment described above by way of example, but instead embraces all the construction variants within the scope of the protection defined by the attached claims.

The invention claimed is:

1. A package for a flexible material, comprising:
a base adapted to receive a flexible material in a planar configuration;
a tubular member having a proximal opening, a distal opening and a lumen extending therethrough, the lumen being configured to receive the flexible material in a folded configuration, said tubular member being disposed in a tray; and
a folding mechanism formed in tray, the folding mechanism configured to fold the flexible material prior to introduction into the tubular member.

2. The packing according to claim 1, further including:

a suture operatively connected to the flexible material; and wherein the folding mechanism has a funnel configured to fold the flexible material for passage of the flexible material into the tubular member.

3. The package according to claim 2, wherein the funnel is positioned adjacent to the distal opening of the tubular member.

4. The package according to claim 1, further comprising a cover such that said cover and tray combine to form a compartment for the tubular member.

5. The package according to claim 2, wherein a suture is disposed through the tubular member and extends through the proximal opening thereof.

6. The packaging according to claim 1, wherein the tubular member is made of a gas-impermeable material.

7. The package according to claim 1, wherein the tubular member includes a proximal gas-tight valve.

8. The package according to claim 2, wherein the funnel comprises at least two spaced apart walls defining a gap therebetween, the gap configured to receive the flexible material.

9. The package according to claim 8, wherein the gap has a width less than a width of the distal opening of the tubular member.

10. The package according to claim 8, wherein the at least two walls are formed by at least two side walls of at least two cylindrical blocks connected to the base.

11. The package according to claim 1, wherein the tray comprises a notch positioned substantially coaxial with a longitudinal axis defined by the tubular member.

12. The package according to claim 11, wherein the notch of the tray is substantially shaped as an inverted "V."

13. The package according to claim 1, further comprising a lid covering the base.

14. The package according to claim 1, wherein tray is formed of a thermoformed synthetic material.

* * * * *